US006699175B2

(12) United States Patent
Miller

(10) Patent No.: US 6,699,175 B2
(45) Date of Patent: Mar. 2, 2004

(54) APPARATUS AND METHOD FOR THE MEASUREMENT OF THE RESISTANCE OF THE URETHRAL SPHINCTER

(75) Inventor: Gary Miller, Milpitas, CA (US)

(73) Assignee: Ethicon, Inc., Somerville, NJ (US)

( * ) Notice: Subject to any disclaimer, the term of this patent is extended or adjusted under 35 U.S.C. 154(b) by 159 days.

(21) Appl. No.: 10/045,245

(22) Filed: Oct. 23, 2001

(65) Prior Publication Data

US 2002/0115906 A1 Aug. 22, 2002

Related U.S. Application Data

(60) Provisional application No. 60/242,554, filed on Oct. 23, 2000.

(51) Int. Cl.[7] .................................................. A61F 2/02
(52) U.S. Cl. ........................................................ 600/30
(58) Field of Search ............................ 600/30, 586, 573, 600/587, 135, 595, 561; 604/141; 128/DIG. 12, 885

(56) References Cited

U.S. PATENT DOCUMENTS

| 4,191,196 | A | | 3/1980 | Bradley et al. |
|---|---|---|---|---|
| 4,484,585 | A | | 11/1984 | Baier |
| 4,612,939 | A | * | 9/1986 | Robertson ............... 600/587 |
| 5,112,344 | A | | 5/1992 | Petros |
| 5,176,148 | A | | 1/1993 | Wiest et al. |
| 5,331,548 | A | | 7/1994 | Rollema et al. |
| 5,449,345 | A | | 9/1995 | Taylor et al. |
| 5,566,680 | A | | 10/1996 | Urion et al. |
| 5,823,972 | A | * | 10/1998 | McRae ............... 600/573 |
| 5,899,909 | A | | 5/1999 | Claren et al. |
| 5,954,696 | A | * | 9/1999 | Ryan ............... 604/141 |
| 6,056,699 | A | | 5/2000 | Sohn et al. |
| 6,273,852 | B1 | | 8/2001 | Lehe et al. |
| 6,447,462 | B1 | | 9/2002 | Wallace et al. |
| 6,461,332 | B1 | | 10/2002 | Mosel et al. |
| 2001/0045355 | A1 | | 11/2001 | Gephart et al. |
| 2002/0123665 | A1 | | 9/2002 | Miller |

FOREIGN PATENT DOCUMENTS

| EP | 0608593 | 8/1994 |
|---|---|---|
| EP | 0878166 | 11/1998 |
| WO | 0023127 | 4/2000 |

OTHER PUBLICATIONS

Petros, P. E. Papa and Ulmsten, U. I., "An Integral Theory and Its Method for the Diagnosis and Management of Female Urinary Incontinence", Scandinavian Journal of Urology and Nephrology Supplement No. 153, Department of Obstetrics and Gynaecology, Sweden, 1993, pp. 1–93.

McLennan, M. T., et al., Article on "Leak–Point Pressure: Clinical Application of Values at Two Different Volumes", International Urogynecology Journal, Springer–Verlag London Limited, 2000, pp. 136–141.

Lane, T.M. and Shah, P.J.R., "Leak–Point Pressures", BJU International No. 86, 2000, pp. 942–949.

Petros, P.E. Papa and Ulmsten, U., Opinion on "An Anatomical Classificaiton—New Paradigm for Management of Urinary Dysfunction in the Female", International Urgynecology Journal, Springer–Verlag London Ltd., 1999, pp. 29–35.

(List continued on next page.)

Primary Examiner—Max F. Hindenburg
Assistant Examiner—Brian Szmal

(57) ABSTRACT

A urinary apparatus includes a catheter system for pressurizing either a bladder cavity or a urethral canal within a female urinary system and an endoscope device for observing a urethral sphincter muscle within the female urinary system for assessing the sling tension of an implant support adapted to restore female urinary continence. The catheter system includes a obturator occlusion member for plugging the urethral canal during the performance of a sling tensioning procedure.

21 Claims, 4 Drawing Sheets

OTHER PUBLICATIONS

Petros, P.E. Papa and Ulmsten, U., "An Anatomical Classification—New Paradigm for Management of Female Lower Urinary Tract Dysfunction", European Journal of Obstetrics & Gynecology and Reproductive Biology No. 80, Elsvier Science Ireland, Ltd, 1998, pp. 87–94.

Sanchez–Doblado, F., et al., Technical Note on "Computerised Analysis of Urological Parameters", Medical and Biological Engineering & Computing, May 1988, pp. 325–327.

Kim, Kyu–Jung, et al., Technical Note on "Principles of Urodynamics Pressure Measurement and Its Implication to Female Continence Function", Journal of Biomechanics No. 31, Elsevier Science Ltd., 1998, pp. 861–865.

Kim, Kyu–Jung, et al., "Vesico–Urethral Pressuregram Analysis of Urethral Function Under Stress", J. Biomechanics, vol. 30, No. 1, Elsevier Science Ltd., 1996, pp. 19–25.

Note, Berlin–Brandenburgicshe, Urogynakologie–Tage, Sept. 20–21, 2002.

Brochure on "Andromeda", Timm Medical Technologies, Inc., Date unknown.

Brochure on Lumax Pro Fiberoptic Cystometry System, Cooper Surgical, Shelton, Conneticut, Oct. 2001.

PCT Search Report, PCT/US01/51015, May, 21, 2002.

* cited by examiner

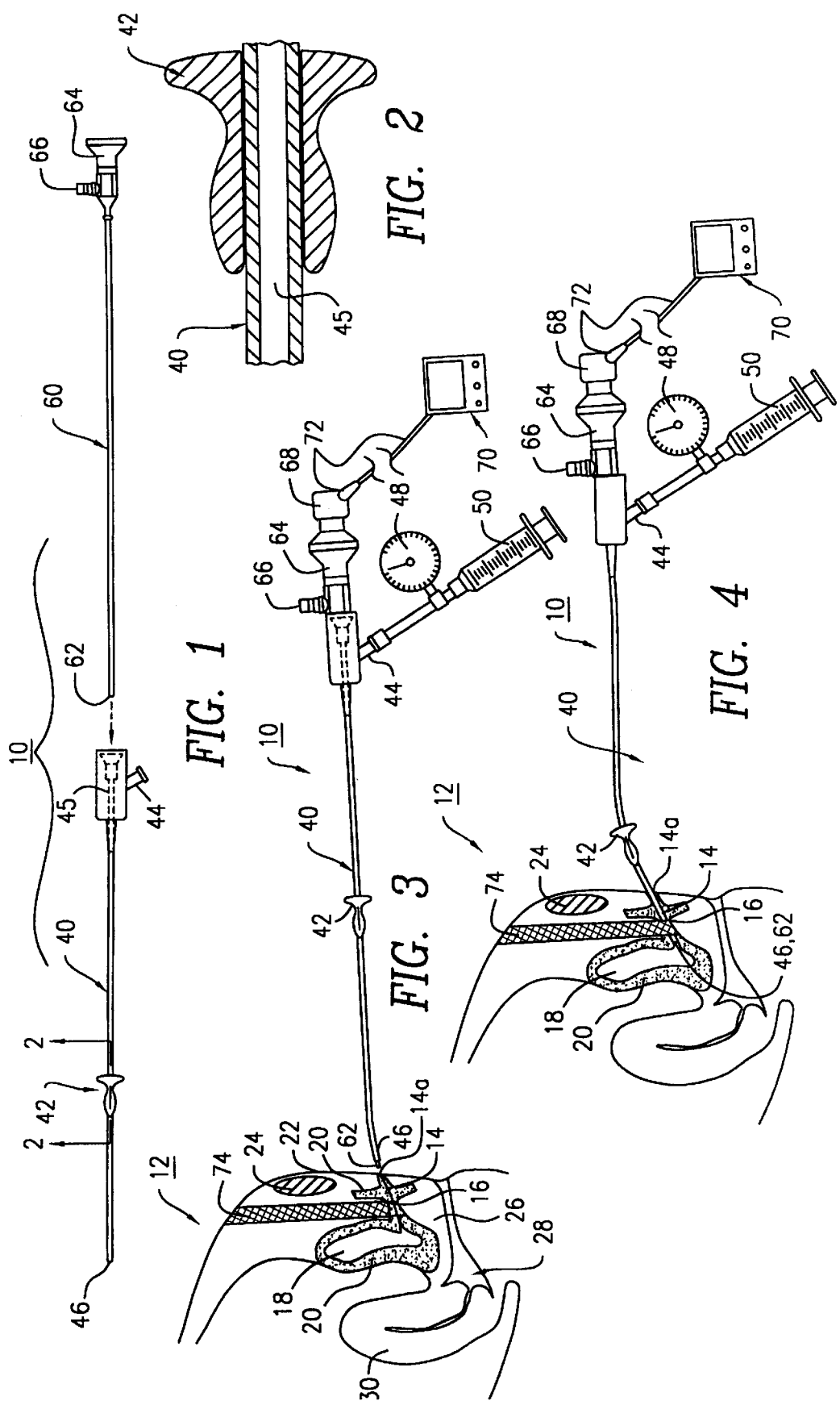

APPARATUS AND METHOD FOR THE MEASUREMENT OF THE RESISTANCE OF THE URETHRAL SPHINCTER

CROSS REFERENCE TO RELATED APPLICATIONS

This is a §111 (a) application relating to a Provisional U.S. Appln. Ser. No. 60/242,554 filed Oct. 23, 2000.

FIELD OF THE INVENTION

The present invention relates generally to a surgical instrument and a method for assessing female urinary incontinence. More particularly, the apparatus and method can be utilized to assess the efficacy of an implant which is adapted to support measure the resistance of the urethral sphincter muscle of the bladder for the purpose of restoring continence to the flow of fluids through the sphincter.

BACKGROUND OF THE INVENTION

Women account for more than 11 million of incontinence cases. Moreover, a majority of women with incontinence suffer from stress urinary incontinence (SUI). Women with SUI involuntarily lose urine during normal daily activities and movements, such as laughing, coughing, sneezing and regular exercise.

SUI may be caused by a functional defect of the tissue or ligaments connecting the vaginal wall with the pelvic muscles and pubic bone. Common causes include repetitive straining of the pelvic muscles, childbirth, loss of pelvic muscle tone and estrogen loss. Such a defect results in an improperly functioning urethra. Unlike other types of incontinence, SUI is not a problem of the bladder.

Normally, the urethra, when properly supported by strong pelvic floor muscles and healthy connective tissue, maintains a tight seal to prevent involuntary loss of urine. When a woman suffers from the most common form of SUI, however, weakened muscle and pelvic tissues are unable to adequately support the urethra in its correct position. As a result, during normal movements when pressure is exerted on the bladder from the diaphragm, the urethra cannot retain its seal, permitting urine to escape. Because SUI is both embarrassing and unpredictable, many women with SUI avoid an active lifestyle, shying away from social situations.

In an effort to help manage female SUI, a physician may surgically place a supportive implant to raise the bladder neck and restore continence. These surgical devices, which are commonly referred to as "slings", are placed in-vivo in a number of ways.

U.S. Pat. No. 5,112,344 describes a method and apparatus for treating female incontinence. The surgical instrument for the application of a filamentary element into the body comprises a tubular shaft having a handle at one end and a flexible needle slidably receivable in the shaft and adapted at one end to receive a filamentary element. The method of treating female incontinence comprises the steps of (1) looping the filamentary element between the wall of the vagina and the rectus abdominis sheath in the anterior wall of the abdomen, whereby the filamentary element passes to each side of the urethra; (2) adjusting the loop to bring the vaginal wall and the urethra into the correct spatial relationship to the pubis, thereby allowing the development of scar tissue between the vaginal wall and the anterior wall of the abdomen pubic symphysis; and (3) removing the filamentary element.

U.S. Pat. No. 5,899,909 discloses a surgical instrument comprising a shank having a handle at one end and connecting means at the other end to receive a pair of curved needles. In practice, a first needle is connected to one end of a tape, while a second needle is connected to an opposite end of the tape. The first needle is then passed into the body via the vagina, through the vaginal wall, and past one side of the urethra. The first needle is then further passed over the pubis and through the abdominal wall, thereby drawing the end of the tape through the body along one side of the urethra. The second needle is also passed into the body via the vagina, through the vaginal wall, and past an opposite side of the urethra. The second needle is then further passed over the pubis and through the abdominal wall, thereby drawing the opposite end of the tape through the body along an opposite side of the urethra, such that the tape forms a loop about the urethra. After the tape is extended over the pubis and through the abdominal wall, it is tightened. The tape ends are then cut at the abdominal wall, leaving the tape implanted in the body.

After placing the sling in the patient, the physician positions the sling with respect to the bladder and urethra. The position required to restore continence is individually determined for each patient by the surgeon. One method to position the sling is to provide the bladder with a predetermined stress or pressure and then the sling is positioned until continence is restored. The stress or pressure applied to the bladder may be provided in two different ways.

If the patient is awake, the physician may instruct the patient to apply abdominal pressure via muscle contraction, such as by coughing. This naturally applied force is considered to be the best gauge for "natural" continence evaluation. However, having the patient awake for this portion of the procedure is clinically inconvenient.

The second method is the most widely used procedure both domestically and internationally. Since the patient is typically anesthetized, requesting the patient to cough or pressurize the bladder is not possible. Consequently, the physician may apply firm positive pressure to the anterior pelvic portion of the body in an effort to induce micturition (i.e., the act of urinating). Pressure is applied repeatedly while the tape or sling is adjusted. The tape is adjusted until only a minor trace of the fluid flow exits the urethra.

The physician may choose to directly pressurize the bladder during ei r of the two procedures described above to more closely simulate the effect of exerting stress on a full or partially filled bladder. Such direct pressurization is achieved by inserting a catheter through the urethral sphincter, by way of the urethral canal, into the bladder, then passing a known volume of fluid into the bladder, then withdrawing the catheter past the urethral sphincter. The remainder of the procedure is carried out as described above. This procedure is necessarily invasive and discomforting to the patient.

When a patient is under general anesthesia and in the supine position, abdominal and skeletal retention muscles are inactive. When manual pressure is applied as in the aforementioned manner, it is believed that the force/pressure focused on the bladder is actually dissipated by the overall relaxed state of the lower abdomen. Gauging tape position and subsequent urodynamics in this manner is extremely dangerous and can lead to adverse conditions, such as urethral restriction, or may maintain incontinence.

Thus, there is a need for an apparatus and method for measuring and monitoring urodynamic flow and pressure variations while positioning the tape in such a way to provide the physician with the exact information needed to ensure optimal clinical safety and efficacy of the tape, as demonstrated by the urinary apparatus of the present invention.

The present invention overcomes the deficiencies of the prior art and provides for an improved urodynamic measurement system that may be used in conjunction with any procedure to treat SUI such as those to suspend the bladder neck or support the urethral sphincter muscle. The measurement system does not require pressurization of the bladder and, therefore, is less invasive than methods which involve direct injection of fluids through the urethral sphincter into the bladder. For illustrative purposes only, the present invention will be discussed in combination with the apparatus and method disclosed in the aforementioned U.S. Pat. No. 5,899,909.

SUMMARY OF THE INVENTION

In accordance with one aspect of the invention, a system for pressurizing a urethral canal within a female urinary system. The urinary apparatus also includes an endoscopic includes an occlusion member for plugging the urethral canal in order to pressurize the urethral canal during the performance of a method to assess urinary function. The method includes the steps of: inserting the occlusion member into the patient's urethral canal at a location proximal to the patient's urethral sphincter: pressurizing the urethral canal with fluid to a pressure level at which the urethral sphincter opens so as to induce reverse leakage back into the bladder; and determining the resistance of the patient's urethral sphincter to the flow of the introduced fluid through the sphincter.

BRIEF DESCRIPTION OF THE DRAWINGS

Further objects, features and advantages of the present invention will become apparent upon consideration of the following detailed description of various exemplary embodiments considered in conjunction with the accompanying drawings, in which:

FIG. 1 is an exploded elevational view of a urinary apparatus constructed in accordance with one exemplary embodiment of the present invention;

FIG. 2 is an enlarged cross-sectional view of the urinary apparatus of FIG. 1 taken along section line 2—2 and looking in the direction of the arrows;

FIG. 3 is a schematic view of a female urinary/reproductive system and the urinary apparatus of FIG. 1, showing a tip portion of the urinary apparatus being inserted into a urethra canal;

FIG. 4 is a view similar to the view of FIG. 3, except that the tip portion of the urinary apparatus is shown in contact with an internal urethral sphincter muscle;

DETAILED DESCRIPTION OF THE EXEMPLARY EMBODIMENTS

Figure 5:
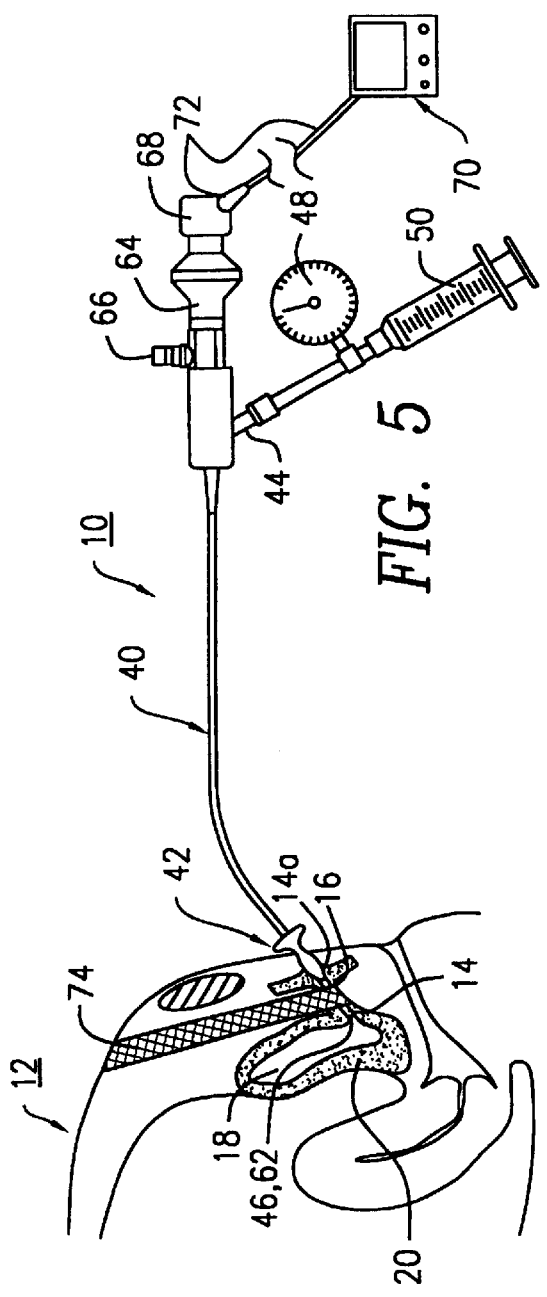
FIG. 5 is a view similar to the view of FIG. 4, except that the tip portion of the urinary apparatus is shown within the lower urethra canal and a slidable obturator occlusion plug is blocking the opening of the urethra canal.

With reference generally to FIGS. 1 through 6, a urinary apparatus 10 is shown which is adapted to be received within a human female urinary system 12. In order to fully understand the advantages of the urinary apparatus 10, a brief overview of the female urinary system 12 is discussed below with particular reference to FIG. 3.

The female urinary system 12 includes an elongated urethral canal 14 having a substantially circular-shaped urethral sphincter muscle 16 attached thereto, and a bladder cavity 18 surrounded by a detrusor muscle 20. The detrusor muscle 20 also surrounds and supports the urethral canal 14. The bladder cavity 18 is in close proximity to the abdominal wall 22, the pubic bone 24, the pelvic floor 26 (levator ani muscle), the vaginal canal 28 and the uterus 30, as depicted in FIG. 3.

Figure 8:
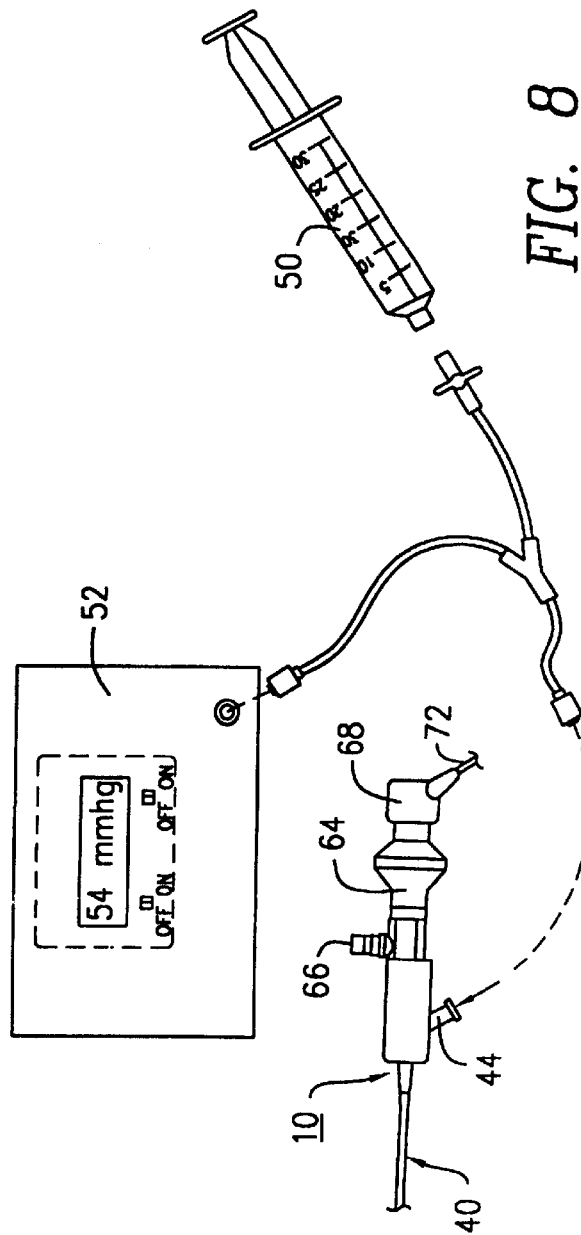
FIG. 8 is a front elevational view of the urinary apparatus of FIG. 6 showing an electronic pressure gauge attached to the occlusion catheter.

Referring again to FIGS. 1 through 6, the urinary apparatus 10 includes a slender and flexible catheter system 40 having a slidable obturator occlusion (plug) member 42 thereon; and a small diameter and flexible endoscope device 60 slidably received within the catheter system 40. The plug member 42 is sized and shaped to fit an entrance opening 14a of the urethral canal 14 and is made from a solid, pliable plastic material. The catheter system 40 has a proximal end which includes an inlet fill port 44 for receiving a fluid, and a distal end which includes a catheter tip section 46 for discharging fluid. The fill port 44 is detachably connected to a pressure gauge 48 and to a syringe member 50. The syringe member 50 contains the fluid for pressurizing the bladder cavity 18 during the assessment procedures for the sling-tension in the treatment of female incontinence, as will be described more fully hereinafter. With reference to FIG. 8, an alternative pressure/measurement device in the form of a urodynamic electronic pressure monitor 52 is used in place of the pressure gauge 48 shown in FIG. 6.

With reference to FIGS. 1 and 3, the endoscope device 60 has a distal end which includes a tip section 62 that can be placed transurethrally, such that the tip section 62 is positioned within the urethral canal 14 of the urinary system 12. The endoscope device 60 also has a proximal end which includes an eye-scope member 64 for viewing in-vivo the urethral canal 14 by the physician (see FIG. 3) and an inlet port 66 for receiving another element such as a light source (i.e., a fiber optic light strand—not shown). The endoscope device 60 can be constructed in accordance with the teachings of co-pending, co-owned U.S. patent application Ser. No. 09/752,259, filed Dec. 29, 2000, which application is incorporated herein by reference.

The endoscope device 60 also includes a video-monitoring scope member 68 for detachably connecting to the eye-scope member 64. The video-monitoring scope member 68 is electronically connected to a video monitor 70 via an electrical line 72 for visually monitoring in-vivo the urethral canal 14 by the medical staff for the assessment and condition of the urethral sphincter muscle 16. This assessment is relative to the tensioning of an inserted tension-free vaginal (mesh) tape (TVT) 74 around the urethral sphincter muscle (bladder neck) 16 in order to determine and ensure the proper tension relationship between the tension-free vaginal tape 74 and the continence level being achieved by the urethral sphincter muscle 16 within the urethral canal 14.

Referring now to FIGS. 3 through 6, the urinary apparatus 10 operates in the following manner. In assembling the urinary apparatus 10, the flexible endoscope device 60 is received within a lumen 45 of the catheter system 40, such that the tip section 46 of the catheter system 40 is substantially aligned with the tip section 62 of endoscope device 60 (see FIG. 3). As shown in FIG. 3, the pressure gauge 48 and syringe member 50 are then connected at the proximal end of the catheter system 40, thereby allowing for the injection of fluid (i.e., a liquid or a gas) out of the tip section 46 from the attached syringe member 50. Additionally, the eye-scope member 64 and the video-monitoring scope member 68 are connected at the proximal end of the endoscope device 60.

The aligned tip sections 46 and 62 of the urinary apparatus 10 are then placed transurethrally within the urethral canal 14, such that the tip sections 46, 62 are positioned on the distal side of the external urethral sphincter muscle 16 adjacent to the bladder cavity 18 of the urinary system 12, as shown in FIG. 4. The diameter of the catheter system 40 is slightly smaller than the natural diameter of the urethral canal 14 during high pressure bladder filling. To eliminate this condition, the obturator occlusion member 42 is slid into place in the urethral canal 14 to act as a luminal plug (see FIG. 5). The catheter system 40 is now positioned in the urethral canal 14, such that the tip section 46 is positioned on the distal side of the urethral sphincter muscle 16 adjacent to the bladder cavity 18 and the obturator occlusion member 42 is positioned on the proximal side of the urethral sphincter muscle 16 adjacent to the urethral canal opening 14a, for pressurizing by fluid of the bladder cavity 18 in a manner which will be described hereinafter.

In order to pressurize the bladder cavity 18, fluid is added to the bladder to a level that is known to be comparable to the pressure experienced during thoracic muscular contracting (stress from coughing). By way of example, the fluid is added to a level as shown on pressure gauge 48 or pressure monitor 52 to a value of about 50 mm Hg (as read off the gauge). The catheter system 40 is then retracted slightly, until the tip sections 46, 62 are repositioned on the proximal side of the closed urethral sphincter muscle 16 (see FIG. 6), while the plug member 42 stays in place. This positioning maintains the bladder pressure of bladder cavity 18 and the firm placement of the plug member 42 within the urethral canal 14. Typically, after the repositioning of tip sections 46, 62 to the proximal side of the urethral sphincter muscle 16, the pressure level within the urethral canal 14 is now zero, as measured by pressure gauge 48 or 52.

Figure 6:
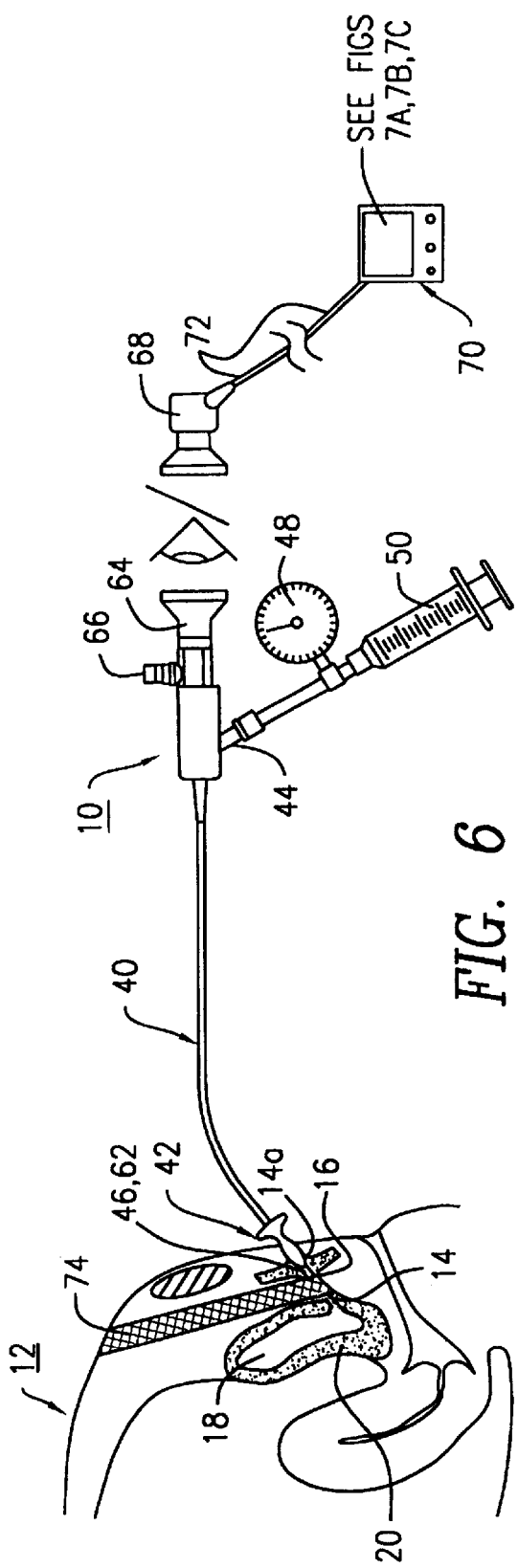
FIG. 6 is a view similar to the view of FIG. 5, except that the urinary apparatus has a pressure gauge, a syringe and a video monitor attached thereto.

The physician is now able to check and assess the tension-free vaginal tape (mesh) 74 for sling-tension (as described in U.S. Pat. No. 5,899,909) by monitoring the orientation of the urethral sphincter muscle 16 via the video-monitoring scope member 68, as presented on the video monitor 70, or as shown through the eye-scope member 64. With reference to FIG. 6, this assessment procedure is done by adding fluid and changing the applied fluid pressure, as shown by pressure gauge 48 or pressure monitor 52. More particularly, fluid is injected from the syringe member 50 and is filled into the urethral canal 14 in order to measure the pressure for opening the urethral sphincter muscle 16 to induce reverse leakage back into the bladder cavity 18.

The physician is now able to perform an in-vivo urodynamic analysis for assessment of the positioning of the tension-free vaginal tape 74 about the urethral sphincter muscle 16. Under direct visualization by the physician, using the eye-scope member 64 or the video-monitoring scope member 68, the urethral support positioning of the tension-free vaginal tape 74 about the urethral sphincter muscle 16 may be adjusted in order to ensure the proper relationship between the tension-free vaginal tape 74 position and continence level as shown in FIGS. 7a, 7b and 7c.

Figure 7A:
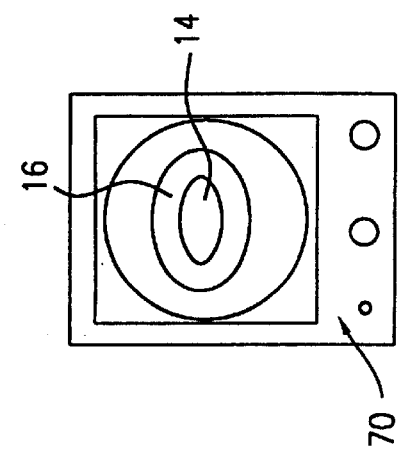
FIG. 7a is a schematic view of the video monitor of the urinary apparatus of FIG. 6 showing the urethral sphincter muscle in a non-functional orientation.

FIG. 7a depicts an in-vivo image indicating a fully opened urethral sphincter muscle 16 which shows no net effect on the incontinence level of the urethral canal 14, thereby indicating to the physician that the tension-free vaginal tape 74 is too loose in placement of the sling tape about the bladder neck of the bladder. This indicates to the physician that the tension-free vaginal tape 74 needs to be tightened about the urethral sphincter muscle 16 in order to restore continence to the urinary system 12.

Figure 7B:
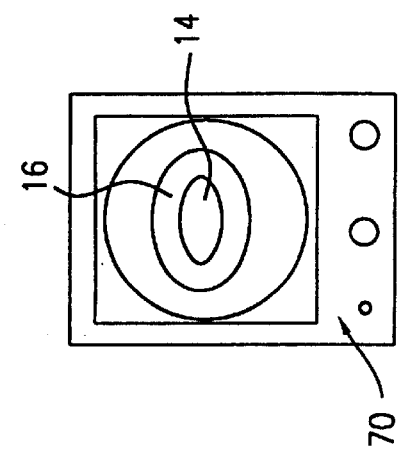
FIG. 7b is a schematic view of the video monitor of the urinary apparatus of FIG. 6 showing the urethral sphincter muscle in a completely closed position.

FIG. 7b depicts an in-vivo image indicating a fully closed urethral sphincter muscle 16 which shows that the placement and positioning of the tension-free vaginal tape (mesh sling tape) 74 has caused a complete and undesired closure of the urethral sphincter muscle 16 within the urethral canal 14. This indicates to the physician that the tension-free vaginal tape 74 is too tight and loosening of the tension-free vaginal tape 74 is therefore necessary in placement of the sling tape about the bladder neck in order to restore patency of the urethral sphincter muscle 16 by the physician.

Figure 7C:
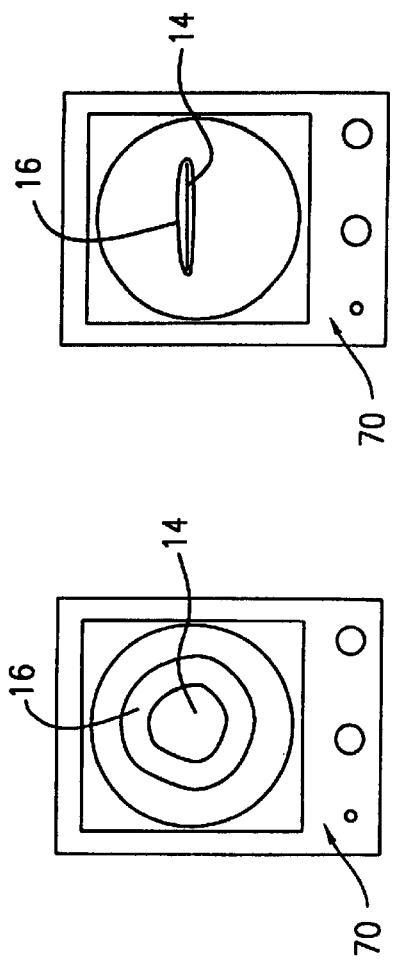
FIG. 7c is a schematic view of the video monitor of the urinary apparatus of FIG. 6 showing the urethral sphincter muscle in a normal and functional orientation.

FIG. 7c depicts an in-vivo image indicating a partially closed urethral sphincter muscle 16 which gives a visualization of this urethral sphincter muscle 16 and the tension-free vaginal tape 74 being in a proper orientation.

The foregoing visualizations, as depicted by FIGS. 7a, 7b and 7c, allow the physician to apply fluid pressure (which may be altered) in order to simulate the effects of applied abdominal pressure to the bladder cavity 18 and to visually check on the effect of continence by the patient. This visualization shows the physician that the tension-free vaginal (mesh) tape 74 was properly positioned relative to the bladder neck of the bladder (see FIG. 6). The physician can now tighten or loosen the tension-free vaginal tape 74 ("tuning the tension-free vaginal mesh tape") by using the tip section 46 of the catheter system 40 on the tension-free vaginal tape 74 in which slack is tightened or removed from the tension-free vaginal tape 74. This tuning of the tension-free vaginal tape 74 is done repeatedly by the physician while repetitiously pressurizing, tensioning the mesh tape 74 and checking patency of the urethral sphincter muscle 16. The viewing of leakage flow ("trickle flow") is slowly and carefully acquired and visualized by the physician, allowing him or her to determine the point at which the urethral sphincter muscle 16 opens to achieve reverse leakage back into the bladder cavity 18 for a particular pressure level as depicted on pressure gauge 48 or pressure monitor 52. After the appropriate adjustment by the physician to the tension-free vaginal tape 74, the "opening pressure" of the newly repaired urethral sphincter muscle 16 may be checked by pressurizing the urethral sphincter muscle 16 from the bladder cavity 18 or from the outflow tract of the urethral sphincter muscle 16 within the urethral canal 14 in order to fill and check for leakage of the fluid in the bladder cavity 18.

During all of the catheter system 40 maneuverings and urethral pressurizing, the diameter of the urethral sphincter muscle 16 (under which the tension-free vaginal tape 74 is positioned), the inherent pressure of the bladder, and/or the urethral outflow tract are always measurable by the use of the urinary apparatus 10. If the tension-free vaginal tape 74 is observed to be too tight, a guide member (not shown) may be placed in the urethra after removing the urinary apparatus 10 at the site of the tension-free vaginal (mesh) tape 74. The guide member is pressed slightly in a downward direction to cause the tension-free vaginal tape 74 to be repositioned. This aforementioned adjustment procedure for the tension-free vaginal tape 74 is then repeated until the appropriate efficacy is achieved which allows the patient to restore continence with her bladder's micturition.

Bearing in mind that pressure ranges may vary from patient to patient and/or from physician to physician, let us assume that, for a particular hypothetical patient, the physician has determined that the appropriate sling tensioning level corresponds to a pressure in a range of from about 22 mmHg to about 48 mmHg, which would indicate a proper orientation and positioning of the tension-free vaginal tape 74 about the urethral sphincter muscle 16. In the process of checking and tuning the tension-free vaginal tape 74 as depicted in FIG. 6, the physician would fill the urethral canal 14 with fluid in small increments from syringe member 50, while simultaneously checking the pressure level of the pressure gauge 48 or 52 to determine when the urethral sphincter muscle 16 opens as viewed in video-monitor 70. Let us further assume that the urethral sphincter muscle 16 opens at a pressure level of 10 mmHg. Bearing in mind that the desired pressure range for sling tensioning is between 22 mmHg to 48 mmHg, the pressure level reading of 10 mmHg would indicate to the physician that the tension-free vaginal tape 74 is too loose and needs to be tightened.

After tightening of the tension-free vaginal tape 74 as described above, the physician would again fill the urethral canal 14 with fluid in small increments from syringe member 50, while simultaneously checking the pressure level of the pressure gauge 48 or 52 to determine when the urethral sphincter muscle 16 opens as viewed in video-monitor 70. In this instance, let us assume that the urethral sphincter muscle 16 now opens at a level of 60 mmHg. Again, bearing in mind that the desired pressure range for sling tensioning is between 22 mmHg to 48 mmHg, the pressure level reading of 60 mmHg would indicate to the physician that the tension-free vaginal tape 74 is too tight and needs to be loosened.

After loosening of the tension-free vaginal tape 74 as described previously, the physician once again fills the urethral canal 14 with fluid in small increments from syringe member 50, while simultaneously checking the pressure level of the pressure gauge 48 or 52 to determine when the urethral sphincter muscle 16 opens as viewed in video monitor 70. Assuming the physician determines that the urethral sphincter muscle 16 now opens at a level of 38 mmHg, this would indicate that the sling tensioning of the tension-free vaginal tape 74 is at a proper level of efficacy for providing continence to the patient for her bladder's micturition.

Figure 9:
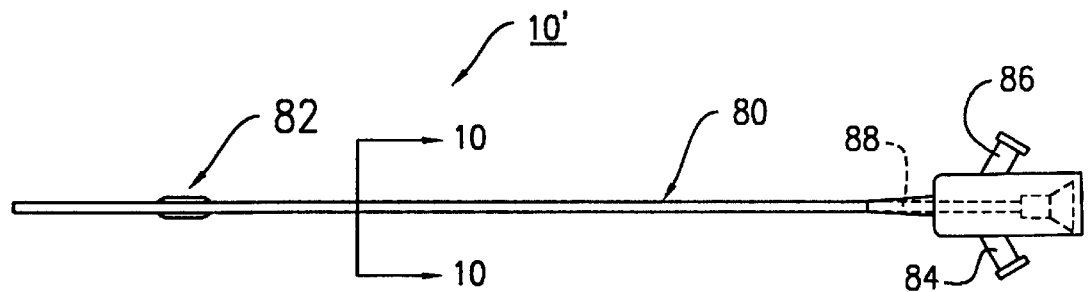
FIG. 9 is a front elevational view of a fixed balloon occlusion catheter constructed in accordance with another exemplary embodiment of the present invention.
Figure 10:
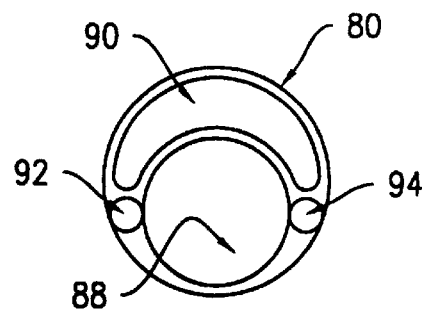
FIG. 10 is an enlarged cross-sectional view of the fixed balloon occlusion catheter of FIG. 9 taken along section line 10—10 and looking in the direction of the arrows.

Referring now to FIGS. 9 and 10, there is shown another exemplary embodiment of a catheter system 80 adapted for use in combination with the endoscope device 60 of FIG. 1, thereby forming a modified urinary apparatus 10'. The catheter system 80 includes a fixed balloon occlusion member 82 used to inflatably block the urethral canal 14 in a manner similar to the obturator occlusion member 42 of FIG. 2. The catheter system 80 has a proximal end which further includes a first inlet fill port 84 for receiving a fluid used to pressurize the bladder cavity 18 (as previously described), and a second inlet fill port 86 for receiving a fluid (liquid or gas) used to inflate and expand the fixed balloon occlusion member 82 with the urethral canal 14 of the urinary system 12. The fixed balloon member 82 is sized and shaped to fit the entrance opening 14a of the urethral canal 14 and is made from an expandable material. As shown in FIG. 10, the catheter system 80 includes an endoscope lumen (opening) 88 for receiving the endoscope device 60 therein, a pressurization lumen 90 for receiving the fluid from the first inlet fill port 84, and a pair of balloon actuation lumens 92, 94 for receiving liquid or gas from the second inlet fill port 86.

With reference to FIGS. 9 and 10, the urinary apparatus 10' operates in exactly the same manner as the urinary apparatus 10 (see FIG. 6), except that the fixed balloon occlusion member 82 is inserted and appropriately positioned within the urethral canal 14. The balloon member 82 is then expanded by liquid or gas from inlet fill port 86 via the balloon actuation lumens 92, 94 of catheter system 80. The physician now proceeds to operate the urinary apparatus 10' as fully described above in connection with the embodiment of FIGS. 1 through 6.

Figure 11:
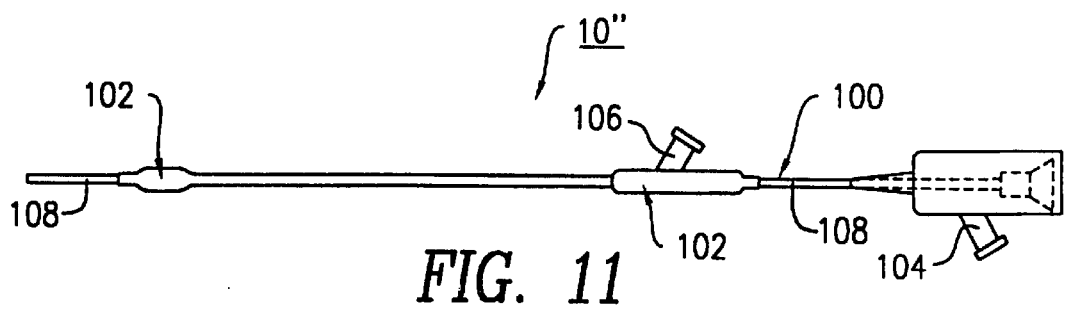
FIG. 11 is a front elevational view of a sliding balloon occlusion catheter constructed in accordance with yet another exemplary embodiment of the present invention.

With reference to FIG. 11, there is shown yet another exemplary embodiment of a catheter system 100 adapted for use in combination with the endoscope device 60 of FIG. 1, thereby forming another modified urinary apparatus 10". The catheter system 100 includes a sliding balloon occlusion member 102 that inflatably blocks the urethral canal 14 in a manner similar to the fixed balloon occlusion member 82 of FIG. 9. The sliding balloon member 102 is sized and shaped to fit the entrance opening 14a of the urethral canal 14 and is made from an expandable material. Additionally, the catheter system 100 has a proximal end which includes a first inlet fill port 104 for receiving a fluid used to pressurize the bladder cavity 18 (as previously described). The sliding balloon occlusion member 102 also has a proximal end which includes a second inlet fill port 106 for receiving fluid material (liquid or gas) therethrough for inflating and expanding the sliding balloon occlusion member 102 within the urethral canal 14 of the urinary system 12. Further, the sliding balloon occlusion member 102 is moveable along a length of the shaft 108 of the catheter system 100.

Still referring to FIG. 11, the urinary apparatus 10" operates in exactly the same manner as the urinary apparatus 10 (see FIG. 6), except that the balloon occlusion member 102 is slidably inserted and appropriately positioned within the urethral canal 14. The balloon member 102 is then inflated/expanded by liquid or gas from inlet fill port 106 of catheter system 100. The physician now proceeds to operate the urinary apparatus 10" as described above in connection with the embodiment of FIGS. 1 through 6.

It should also be understood that the embodiments described herein are merely exemplary and that a person skilled in the art may make many variations and modifications without departing from the spirit and scope of the invention. For instance, pressure can be supplied to the bladder cavity 18 and the urethral canal 14 by means of a hydrostatic pressure head, such as a hanging fluid bottle/bag and an IV administration tubing set, which would replace the syringe member 50. In such a case, the applied pressure would still be measured by a suitable pressure gauge, such as an electronic pressure gauge or an analog tube gauge. All such variations and modifications are intended to be included within the scope of the invention as defined in the appended claims.

What is claimed is:

1. An apparatus for assessing urinary function, comprising:
    pressurizing means for pressurizing a patient's urethral canal at a location proximal to the patient's urethral sphincter until the urethral sphincter opens, whereby fluid may flow from the patient's urethral canal into the patient's bladder and
    measuring means for measuring the resistance of the urethral sphincter to fluid flow during its pressurization by said pressurizing means.

2. The apparatus according to claim 1, wherein the measuring means is a pressure measuring means for measuring pressure within the urethral canal during pressurizing.

3. The apparatus according to claim 2, wherein the measuring means includes a pressure gauge.

4. The apparatus according to claim 1, wherein the pressurizing means includes delivering means for delivering fluid into the urethral canal, and an occluding means for substantially occluding the urethral canal to thereby prevent fluid flow into or out of the urethral canal other than through the occluding means.

5. The apparatus according to claim 4, wherein the occluding means has a channel therethrough through which fluid from the delivering means may pass.

6. The apparatus according to claim 5, wherein the delivering means includes a fluid source and an infusion means for infusing fluid from the fluid source, through the occluding means channel and into the urethral canal.

7. The apparatus according to claim 6, wherein the infusion means is a syringe.

8. The apparatus according to claim 4, wherein the delivering means includes a hanging fluid source that produces a hydrostatic pressure head.

9. An apparatus for assessing urinary function, comprising:
    an occlusion member having a channel therethrough and dimensioned for insertion into a patient's urethral canal at a location proximal of to the patient's urethral sphincter, and dimensioned to substantially block fluid flow between the occlusion member and an inner wall of the urethral canal when so inserted;
    a fluid delivery system including a fluid conduit in fluid communication with the occlusion member channel, the fluid delivery system being capable of delivering fluid from a fluid source through the occlusion member channel and into the urethral canal proximal to the urethral sphincter; and
    a measurement assembly for measuring the resistance of the urethral sphincter as fluid from the fluid delivery system is delivered into the urethral canal.

10. The apparatus according to claim 9, wherein the measurement assembly further comprises a pressure detector for measuring a pressure within the urethral canal proximal to the urethral sphincter as fluid is delivered.

11. The apparatus according to claim 10, wherein the measurement assembly further includes a pressure display electrically coupled to the pressure sensor for displaying pressure information detected by the pressure detector.

12. The apparatus according to claim 10, wherein the pressure detector is in fluid communication with the urethral sphincter proximal to the urethral sphincter when the occlusion member is inserted therein.

13. The apparatus according to claim 12, wherein the pressure detector includes a pressure gauge.

14. The apparatus according to claim 9, wherein the fluid source forms part of the fluid delivery system, and the fluid delivery system further comprises a syringe member for infusing fluid from the fluid source, through the fluid conduit and occlusion member channel and into the patient's urethral canal.

15. The apparatus according to claim 9, wherein the fluid source is a hanging fluid source that produces a hydrostatic pressure head.

16. A method for assessing urinary function, comprising the steps of:
    inserting an occlusion member having a channel therethrough into a patient's urethral canal at a location proximal to the patient's urethral sphincter, the occlusion member being dimensioned to substantially prevent fluid flow between the occlusion member and an inner wall of the urethral canal;
    introducing fluid through the occlusion member channel and into the patient's urethral canal proximal to the urethral sphincter until the urethral sphincter opens to thereby permit fluid to flow from the patient's urethral canal into the patient's bladder; and
    determining a resistance of the patient's urethral sphincter to the introduced fluid.

17. The method according to claim 16, wherein the determining step further comprises determining a pressure within the urethral canal proximal to the urethral sphincter as fluid is introduced therein, and determining a pressure at which the urethral sphincter opens.

18. The method according to claim 16, wherein the determining step further comprises determining a pressure at which the urethral sphincter opens.

19. The method according to claim 18, wherein the pressure is determined using a pressure gauge.

20. The method according to claim 16, wherein the introducing step comprises introducing fluid from a fluid source using a syringe device.

21. The method according to claim 16, wherein the I, step comprises coupling a first end of a tubing conduit to a hanging fluid source that produces a hydrostatic pressure head, and coupling a second end of the tubing conduit to the occlusion member channel so as to be in fluid communication therewith.

* * * * *

UNITED STATES PATENT AND TRADEMARK OFFICE
CERTIFICATE OF CORRECTION

PATENT NO. : 6,699,175 B2
DATED : March 2, 2004
INVENTOR(S) : Gary Miller

It is certified that error appears in the above-identified patent and that said Letters Patent is hereby corrected as shown below:

<u>Column 10,</u>
Line 49, please delete "I," and insert therefore -- introducing --

Signed and Sealed this

Fourteenth Day of September, 2004

JON W. DUDAS
*Director of the United States Patent and Trademark Office*